US012721970B2

(12) United States Patent
Kajiwara et al.

(10) Patent No.: US 12,721,970 B2
(45) Date of Patent: Sep. 1, 2026

(54) TRAPPING BALLOON CATHETER

(71) Applicant: Togo Medikit Co., Ltd., Tokyo (JP)

(72) Inventors: Yasuaki Kajiwara, Tokyo (JP); Tomikazu Fukumoto, Tokyo (JP)

(73) Assignee: TOGO MEDIKIT CO., LTD., Tokyo (JP)

( * ) Notice: Subject to any disclaimer, the term of this patent is extended or adjusted under 35 U.S.C. 154(b) by 573 days.

(21) Appl. No.: 18/257,005

(22) PCT Filed: Dec. 20, 2021

(86) PCT No.: PCT/JP2021/047037
§ 371 (c)(1),
(2) Date: Jun. 12, 2023

(87) PCT Pub. No.: WO2022/172600
PCT Pub. Date: Aug. 18, 2022

(65) Prior Publication Data

US 2024/0042172 A1 Feb. 8, 2024

(30) Foreign Application Priority Data

Feb. 12, 2021 (JP) ................................ 2021-020512

(51) Int. Cl.
*A61M 25/01* (2006.01)
*A61M 25/10* (2013.01)

(52) U.S. Cl.
CPC ........ *A61M 25/0105* (2013.01); *A61M 25/10* (2013.01)

(58) Field of Classification Search
CPC ............. A61M 25/0105; A61M 25/10; A61M 25/104; A61M 2025/0006;
(Continued)

(56) References Cited

U.S. PATENT DOCUMENTS 5,269,759 A * 12/1993 Hernandez ........... A61M 25/09 604/529
5,388,590 A * 2/1995 Horrigan .......... A61M 25/0169 600/585
(Continued)

FOREIGN PATENT DOCUMENTS

JP 2-277465 A 11/1990
JP 2011-120802 A 6/2011
(Continued)

OTHER PUBLICATIONS

International Search Report from PCT/JP2021/046143 Feb. 1, 2022, 2 pgs.
(Continued)

*Primary Examiner* — Theodore J Stigell
(74) *Attorney, Agent, or Firm* — Tutunjian & Bitetto, P.C.

(57) ABSTRACT

The trapping balloon catheter includes a catheter shaft formed to a predetermined total length L from a rear end connected to a hub to a tip. A balloon is provided in a tip region of the catheter shaft and urges and fixes a guide wire to an inner peripheral surface of a guiding catheter by being expanded in a lumen of the guiding catheter. A stopper is provided on an outer peripheral surface of the catheter shaft and is capable of adjusting a length (effective length) in which the trapping balloon catheter is inserted into the lumen of the guiding catheter, by changing a locking position.

5 Claims, 14 Drawing Sheets

(58) Field of Classification Search
CPC .. A61M 2025/0008; A61M 2025/0293; A61M 2025/0681; A61M 2025/09125
See application file for complete search history.

(56) References Cited

U.S. PATENT DOCUMENTS

| | | | | |
|---|---|---|---|---|
| 5,395,389 | A * | 3/1995 | Patel | A61M 25/0169 604/96.01 |
| 6,270,465 | B1 * | 8/2001 | Keith | A61M 25/0105 600/585 |
| 8,109,953 | B1 * | 2/2012 | King, III | A61B 17/22 606/191 |
| 10,080,874 | B2 | 9/2018 | Fuller et al. | |
| 2016/0296732 | A1 * | 10/2016 | Fuller | A61M 25/09 |
| 2017/0197063 | A1 * | 7/2017 | Ahmed | A61M 25/09 |

FOREIGN PATENT DOCUMENTS

| | | | |
|---|---|---|---|
| JP | 2016-124 | A | 1/2016 |
| JP | 2019-17738 | A | 2/2019 |

OTHER PUBLICATIONS

Japanese 1st Office Action for JP2021-20512, Issued Apr. 30, 2021, 11 pgs.

Japanese 2nd Office Action for JP2021-20512, Issued Sep. 17, 2021, 9 pgs.

Kaenka Corporation; Coronoary Catheter Replacement Catherter; Product description; accessed from from company website Jun. 12, 2023.

* cited by examiner 3
7
2a
2
2c
M2
1
6b
6
6k
M1
5a
5
5b
2b
L1
L2
L
L3

TRAPPING BALLOON CATHETER

CROSS-REFERENCE TO RELATED APPLICATIONS

This U.S. National Stage application claims the benefit and priority under 35 U.S.C. § 371 of PCT/JP2021/047037 filed on Dec. 20, 2021, which claims the benefit and priority of Japanese Patent application No. 2021-020512 filed on Feb. 12, 2021, the disclosures of which are incorporated herein by reference in their entireties.

TECHNICAL FIELD

The present invention relates to a trapping balloon catheter. Specifically, the present invention relates to a trapping balloon catheter used to assist insertion and removal of a catheter in percutaneous transluminal coronary angioplasty (PTCA) which is a less invasive procedure using a catheter.

BACKGROUND

Conventionally, this type of trapping balloon catheter including a catheter shaft connected with a hub and a balloon placed in the top end region of the catheter shaft, the balloon inflating in the lumen of a guiding catheter to bias and fix a guide wire to the inner periphery of the guiding catheter is known (Non-Patent Document 1). However, the trapping balloon catheter disclosed in Non-Patent Document 1 does not have a length adjustment function that adjusts the immersion length (effective length) into the lumen of the guiding catheter. Therefore, different types of trapping balloon catheters with different effective lengths have been adaptably prepared for guiding catheters with different effective lengths. This leads to a problem of cost increase as a whole.

As disclosed in Patent Document 1, a trapping balloon catheter that has a length adjustment function with a capability of adjusting the immersion length (effective length) into the lumen of a guiding catheter is proposed. The length adjustment function of the trapping balloon catheter disclosed in Patent Document 1 has a slidable member slidably placed along a catheter shaft between a first position indicating the first working length (first effective length) of the catheter shaft and a second position indicating the second working length (second effective length) of the catheter shaft; a first stop part placed to the distal end region of the slidable member; a second stop part placed to the proximal end region of the slidable member; a reduced-diameter distal end region with which the second stop part engages when the slidable member is at the first position; and a landing region with which the second stop part engages when the slidable member is at the second position.

DOCUMENT IN THE EXISTING ART

Non-Patent Document

Non-Patent Document 1: KANEKA CORPORATION, “KANEKA EXCHANGE DEVICE CO-N1”, Specially controlled medical device, Catheter for exchange of coronary artery catheters, Revised on August, 2020 (5th edition), [online], Retrieved on Dec. 4, 2020, Internet <URL; https://www.info.pmda.go.jp/ygo/pack/200095/22400BZX00362000_A_01_04/>

Patent Document

Patent Document 1: U.S. Ser. No. 10/080,874 B

SUMMARY

The Technical Problem Solved by the Disclosure

The constitution of the trapping balloon catheter disclosed in Patent Document 1 has a problem in which the mechanism of the length adjustment function is complex and increases the manufacturing cost. Since the catheter shaft of the trapping balloon catheter is very thin, the back-and-forth operation and the rotating (torque) operation by pushing, etc., is difficult. However, Patent Document 1 does not disclose a mechanism facilitating these operations.

An objective of the present invention is to cost-effectively provide a trapping balloon catheter with adaptability for guiding catheters with different effective lengths and excellent operability and capability.

Solution for Solving the Technical Problem

According to the first aspect of the present invention, a trapping balloon catheter for assisting insertion and/or removal of a catheter, the trapping balloon catheter being inserted in a lumen of a guiding catheter, the trapping balloon catheter biasing and fixing a guide wire to the inner periphery of the guiding catheter, includes:

a catheter shaft being formed to have a predetermined total length L from the back end to the front end connected with a hub through a strain relief;

a balloon being placed in the top end region of the catheter shaft, the balloon inflating in the lumen of the guiding catheter to bias and fix the guide wire to the inner periphery of the guiding catheter;

a through-hole penetrating the catheter shaft;

a lock mechanism being placed on the outer periphery of the catheter shaft, the lock mechanism being locked to fix at a predetermined position in the longitudinal direction of the catheter shaft and a position which the strain relief enters, the lock mechanism being unlocked to slidably move on the outer periphery of the catheter shaft in the longitudinal direction;

a gripper being gripped in back-and-forth moving operation and rotating operation of the trapping balloon catheter;

an abutting part abutting the back end of a connection device placed at the base end of the guiding catheter and/or the base end of the guiding catheter; and a stopper adjusting the insertion length of the trapping balloon catheter into the lumen of the guiding catheter by changing the locking position.

In the present invention, various examples of a catheter to be inserted and removed include a penetration catheter, a micro catheter, and a balloon catheter. In the present invention, examples of a connection device placed at the base end of the guiding catheter include a Y-shaped connector and a T-shaped connector.

The trapping balloon catheter according the first aspect of the present invention has the following function effects. The trapping balloon catheter according to the first aspect of the present invention has a stopper being placed on the outer periphery of the catheter shaft, the stopper (length adjusting function) adjusting the insertion length (effective length) of the trapping balloon catheter into the lumen of the guiding catheter by changing the locked position, Accordingly, the trapping balloon catheter is adaptable for guiding catheters with different effective lengths. As the result, the trapping balloon catheter can attempt to decrease the cost as a whole without the need to increase the type of trapping balloon catheter with different effective lengths. The stopper as the length adjustment function is simply provided with a lock mechanism being locked to fix at a predetermined position in the longitudinal direction of the catheter shaft, the lock mechanism being unlocked to slidably move on the outer periphery of the catheter shaft in the longitudinal direction; a gripper being gripped in back-and-forth moving operation and rotating operation of the trapping balloon catheter; and an abutting part abutting the back end of a connection device placed at the base end, etc., of the guiding catheter. Accordingly, the trapping balloon catheter can suppress the manufacturing cost. Since the catheter shaft of the trapping balloon catheter is very thin, the back-and-forth operation and the rotating (torque) operation by pushing, etc., is difficult. However, these operations are facilitated by gripping the gripper of the stopper. Therefore, according to the first aspect of the present invention, the trapping balloon catheter can be adapted for guiding catheters with different effective lengths, and the trapping balloon catheter with excellent operability can be provided at low cost.

Furthermore, the trapping balloon catheter according to the first aspect of the present invention can prevent the balloon of the trapping balloon catheter from popping out from the top end of the guiding catheter because the stopper stops at the proximal part of the guiding catheter. As the result, the function of the trapping balloon catheter that biases and fixes a guide wire to the inner periphery of the guiding catheter can always be fulfilled. Moreover, according to the first aspect of the present invention, the stopper is provided with a through-hole into which the catheter shaft penetrates so that the stopper can always be maintained on the catheter shaft. As the result, the stopper can be prevented from falling off from the catheter shaft and always be equipped. Moreover, according to the first aspect of the present invention, the effective length can be secured by fixing the stopper to a position which the strain relief enters when arteriosclerotic developed in a femoral artery, an iliac artery, a popliteal artery, a below-the-knee artery, etc., is treated.

The trapping balloon catheter according to the first aspect of the present invention preferably has any one of the second to fifth aspects of the present invention.

According to the second aspect of the present invention, in the trapping balloon catheter according to the first aspect of the present invention, the diameter of the through-hole of the stopper is from 0.5 to 1.0 mm. According to the preferable second aspect of the present invention, the distance between the inner periphery of the through-hole of the stopper and the outer periphery of the catheter shaft can be an appropriate length, and the stopper can be not unstably but smoothly moved.

According to the third aspect of the present invention, in the trapping balloon catheter according to the first or the second aspect of the present invention, the length of a part of the abutting part where the length from the through-hole to the outer edge is maximized is larger than the inner radius of the back end of the connection device placed at the base end of the guiding catheter and/or the inner radius of the base end of the guiding catheter. According to the preferable third aspect of the present invention, the stopper can surely abut the back end of the connection device placed at the base end of the guiding catheter or the base end of the guiding catheter. As the result, the stopper does not physically enter the connection device so that the stopper function of the stopper can be more surely fulfilled.

According to the fourth aspect of the present invention, in the trapping balloon catheter according to any one of the first to the third aspects of the present invention, the gripper has a length of 5 mm or more in the longitudinal direction. According to the fourth aspect of the present invention, the back-and-forth operation and the rotating (torque) operation by pushing, etc., of the trapping balloon catheter is facilitated so that the operability of the trapping balloon catheter can be more improved.

According to the fifth aspect of the present invention, in the trapping balloon catheter according to any one of the first to the fourth aspects of the present invention, a position with a predetermined length L1 from the top end of the catheter shaft is marked with the marker M1, and a position with a predetermined length L2 which is longer than the predetermined length L1 from the top end of the catheter shaft is marked with the marker M2. According to the fifth aspect of the present invention, the insertion length (effective length) of the trapping balloon catheter into the lumen of the guiding catheter can be easily changed only by moving and fixing the top end of the stopper to either the marker M1 or M2.

Technical Effect

Therefore, according to the present invention, the trapping balloon catheter can be adapted for guiding catheters with different effective lengths, and the trapping balloon catheter with excellent operability can be provided at low cost.

BRIEF DESCRIPTION OF THE DRAWINGS

(FIG. 8A The balloon is deflated. FIG. 8B The balloon is inflated.)

(FIG. 11A The stopper is unlocked. FIG. 11B The stopper is locked.)

(FIG. 12A The stopper is unlocked. FIG. 12B The stopper is locked.)

DETAILED DESCRIPTION OF THE EMBODIMENTS

The present invention will be more specifically described below with reference to the preferable embodiments. However, these are illustrative only, and the present invention is not limited thereto.

Configuration of Trapping Balloon Catheter

The configuration of the trapping balloon catheter according to one embodiment of the present invention is described below with reference to FIGS. 1 to 8A-8B. The size values (inside diameter, outside diameter, and length) and the materials of each member described below are just one example. The present invention is not limited to these values or materials.

Figure 1:
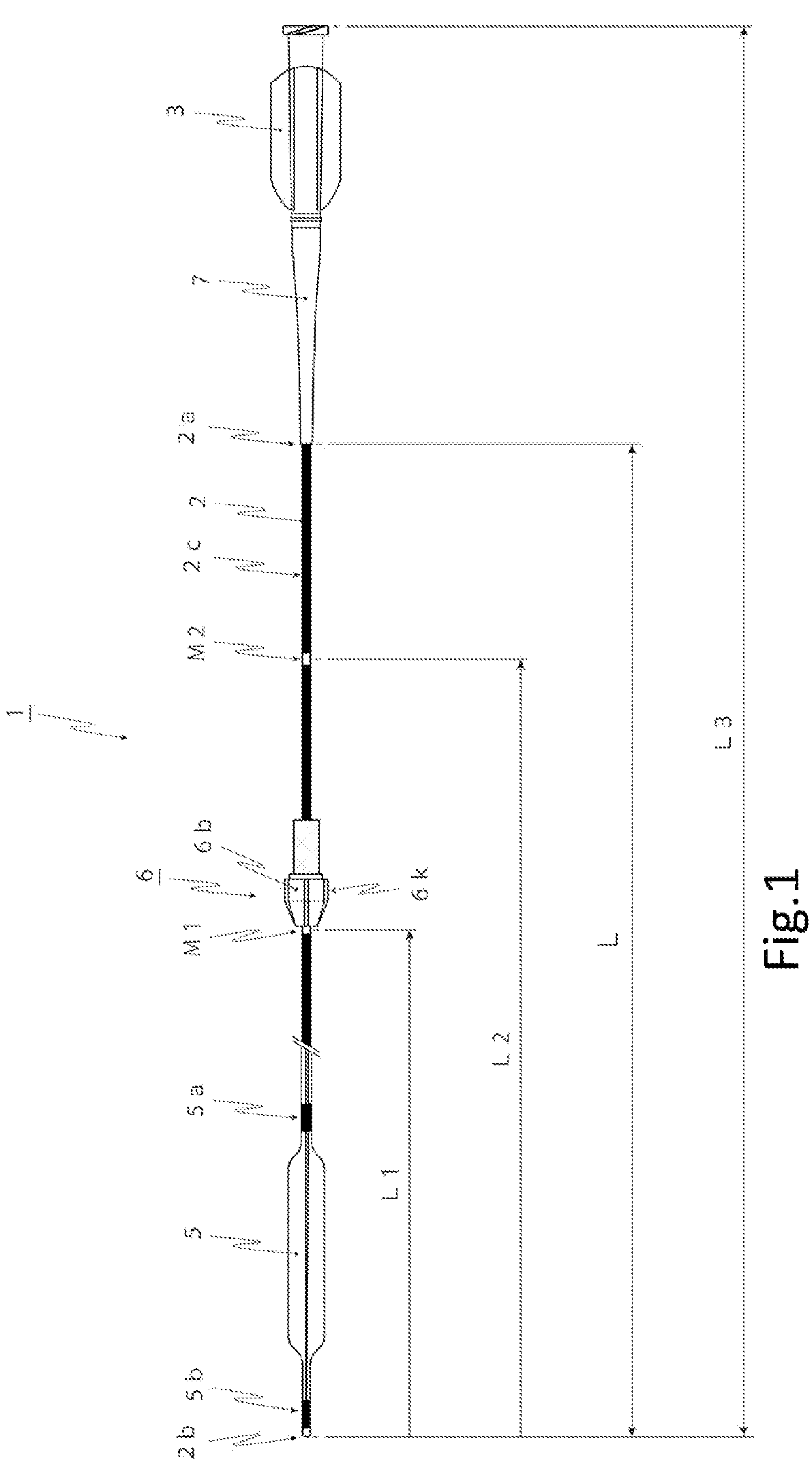
FIG. 1 is a side view illustrating the schematic configuration of the trapping balloon catheter according to one embodiment of the present invention (in the state where the stopper is fixed at a position with a predetermined length L1 from the top end of the catheter shaft).
Figure 2:
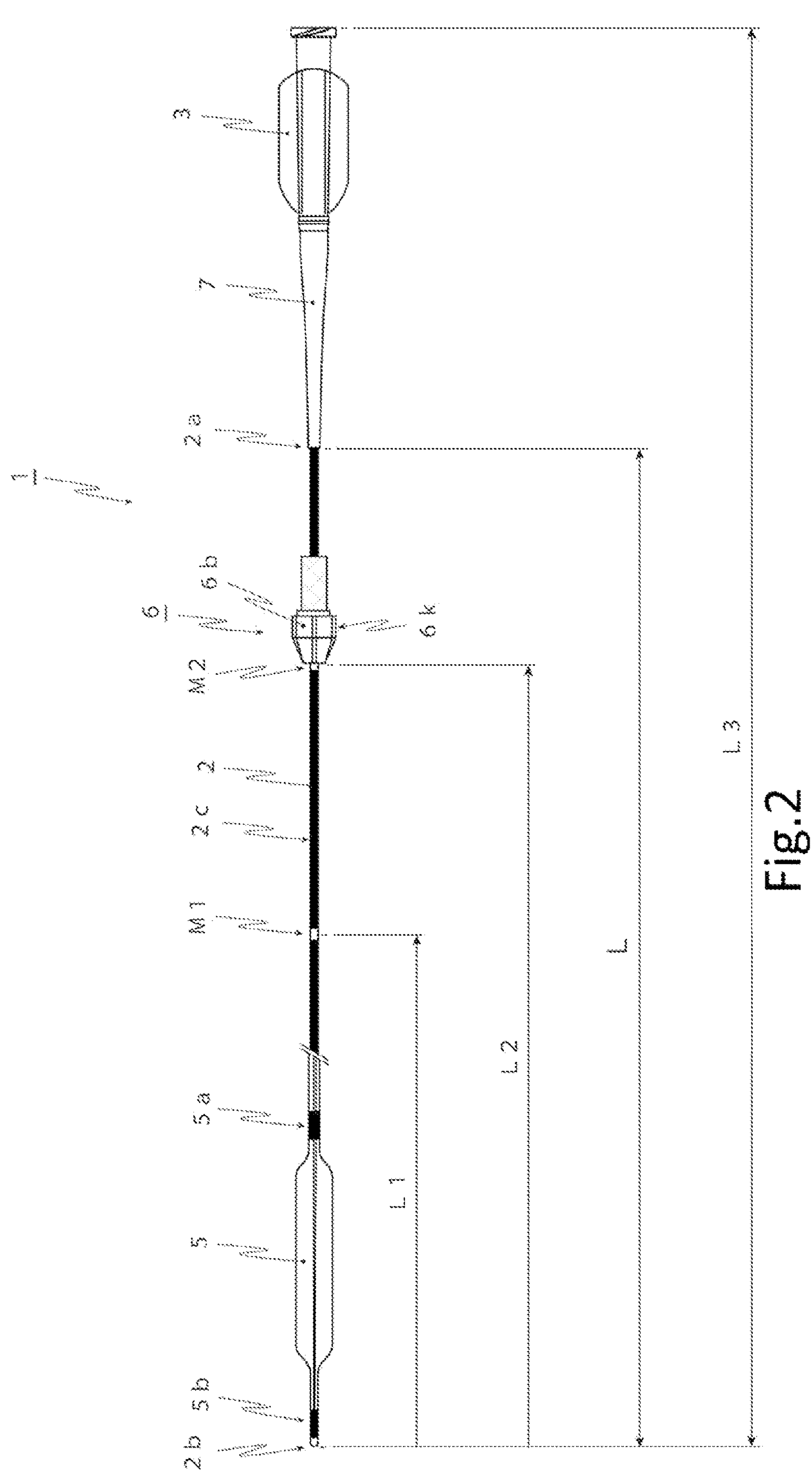
FIG. 2 is a side view illustrating the schematic configuration of the trapping balloon catheter according to one embodiment of the present invention (in the state where the stopper is fixed at a position with a predetermined length L2 which is longer than the predetermined length L1 from the top end of the catheter shaft).
Figure 3:
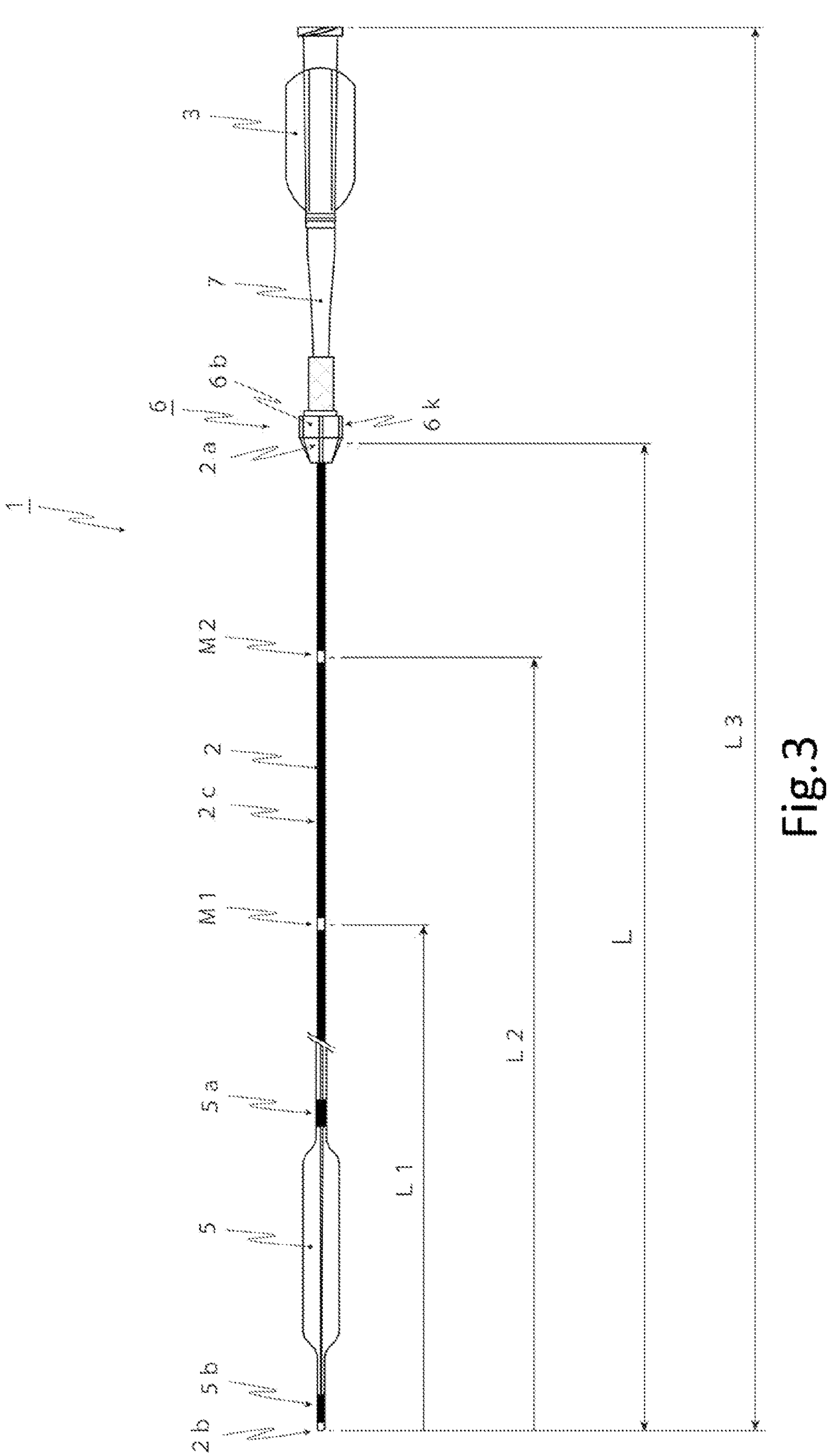
FIG. 3 is a side view illustrating the schematic configuration of the trapping balloon catheter according to one embodiment of the present invention (in the state where the stopper is fixed at a position which the strain relief enters).
Figures 8A, 8B:
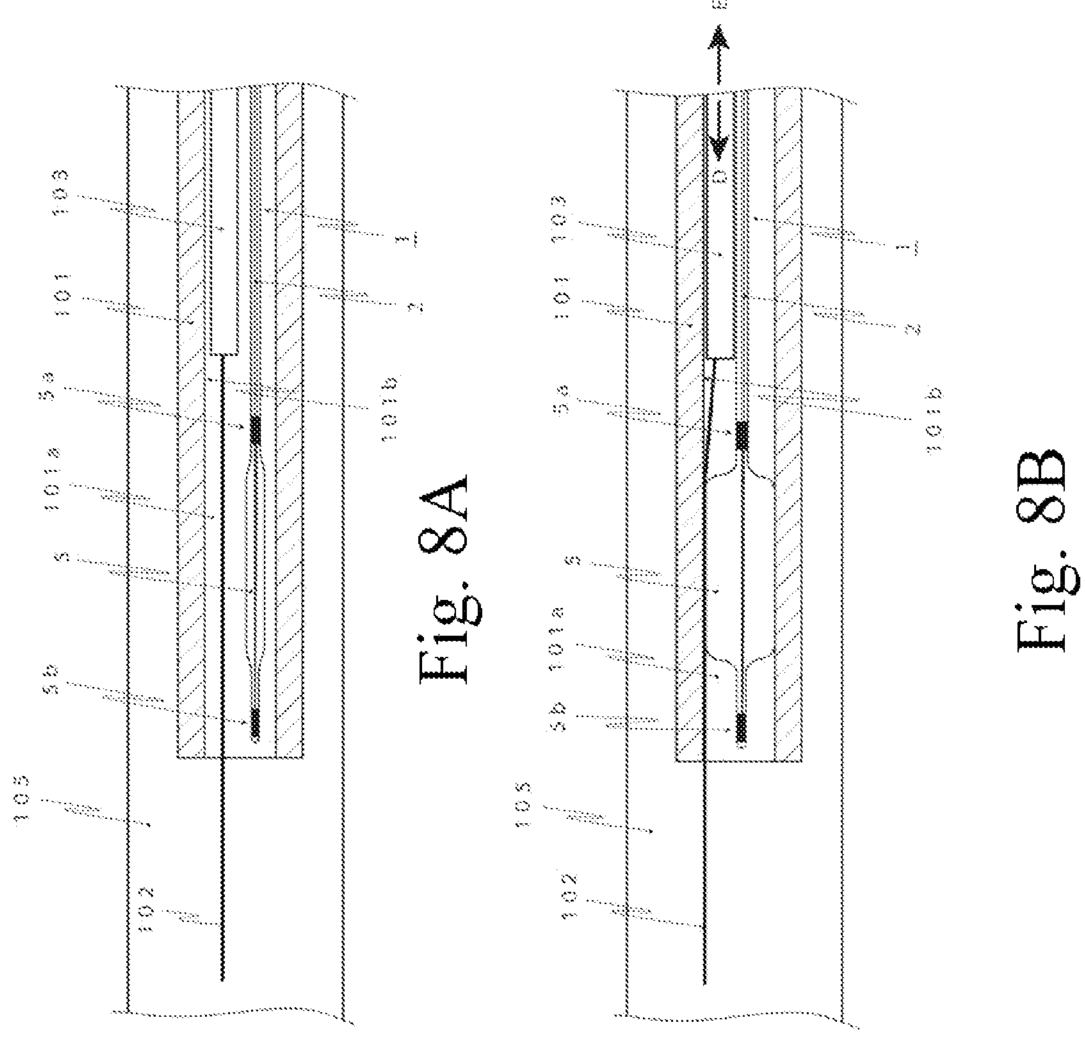
FIGS. 8A-8B are an enlarged cross-sectional side view to explain how to bias and fix a guide wire to the inner periphery of the guiding catheter by using the trapping balloon catheter according to one embodiment of the present invention.

While the trapping balloon catheter 1 shown in FIGS. 1 to 3 is inserted in a lumen 101*a* of a guiding catheter 101, the trapping balloon catheter 1 biases and fixes a guide wire 102 to the inner periphery 101*b* of the guiding catheter 101 to assist insertion and/or removal of various catheters 103 such as a penetration catheter, a micro catheter, and a balloon catheter (refer to the arrows D, E of FIG. 8B). The reference numeral 105 in FIGS. 8A-8B to 10H-10L shows a blood vessel.

As shown in FIGS. 1 to 3, the trapping balloon catheter 1 has a catheter shaft 2, a balloon 5 placed in the top end region of the catheter shaft 2, and a stopper 6 placed on the outer periphery 2*c* of the catheter shaft 2. A lumen for balloon inflation (not shown in the attached drawings) is formed on the catheter shaft 2 along the axial direction. The catheter shaft 2 is formed to have a predetermined total length L (effective length) from the back end 2*a* to the front end 2*b* connected with a hub 3 through a strain relief (anti-kink protector). The balloon 5 is inflatable by introducing a balloon inflating medium from the base end opening of the hub 3. The balloon 5 biases and fixes the guide wire 102 to the inner periphery 101*b* of the guiding catheter 101 by inflating in the lumen 101*a* of the guiding catheter 101 (refer to FIG. 8B). X-ray impermeable markers 5*a* and 5*b* are provided in the outside of the both ends (the proximal side and the distal side) of the balloon 5 to allow the user to confirm the position of the balloon 5 under X-ray illumination.

As shown in FIGS. 1 to 5, the stopper 6 is provided with a gripper member 6*a* that is formed in a thick-walled, approximately cylindrical shape, a tightening cap 6*b* that is detachably covered at and spirally attached to the top end of the gripper member 6*a*, and a tightening elastic member 6*c*. The back side of the gripper member 6*a* functions as a gripper gripped (when used as a torque device) for the back-and-forth movement operation and the rotating (torque) operation by pushing, etc., of the trapping balloon catheter 1. The base end 6*i* of the tightening cap 6*b* described later can function as a gripper. Moreover, a flange 6*g* that restricts the movement (refer to the arrow C of FIG. 4) caused by spirally attaching the tightening cap 6*b* is formed in the center front end of the gripper member 6*a*. In the tightening elastic member 6*c*, the cylindrical part of a four-way collet chuck is set in the front of the gripper member 6*a*, and the split-in-four head (expandable and shrinkable part) as a radially expanding and shrinking part in the front of the four-way collet chuck projects from the front end of the gripper member 6*a*. The taper wall 6*h* is formed on the front inner periphery of the tightening cap 6*b*.

Figure 5:
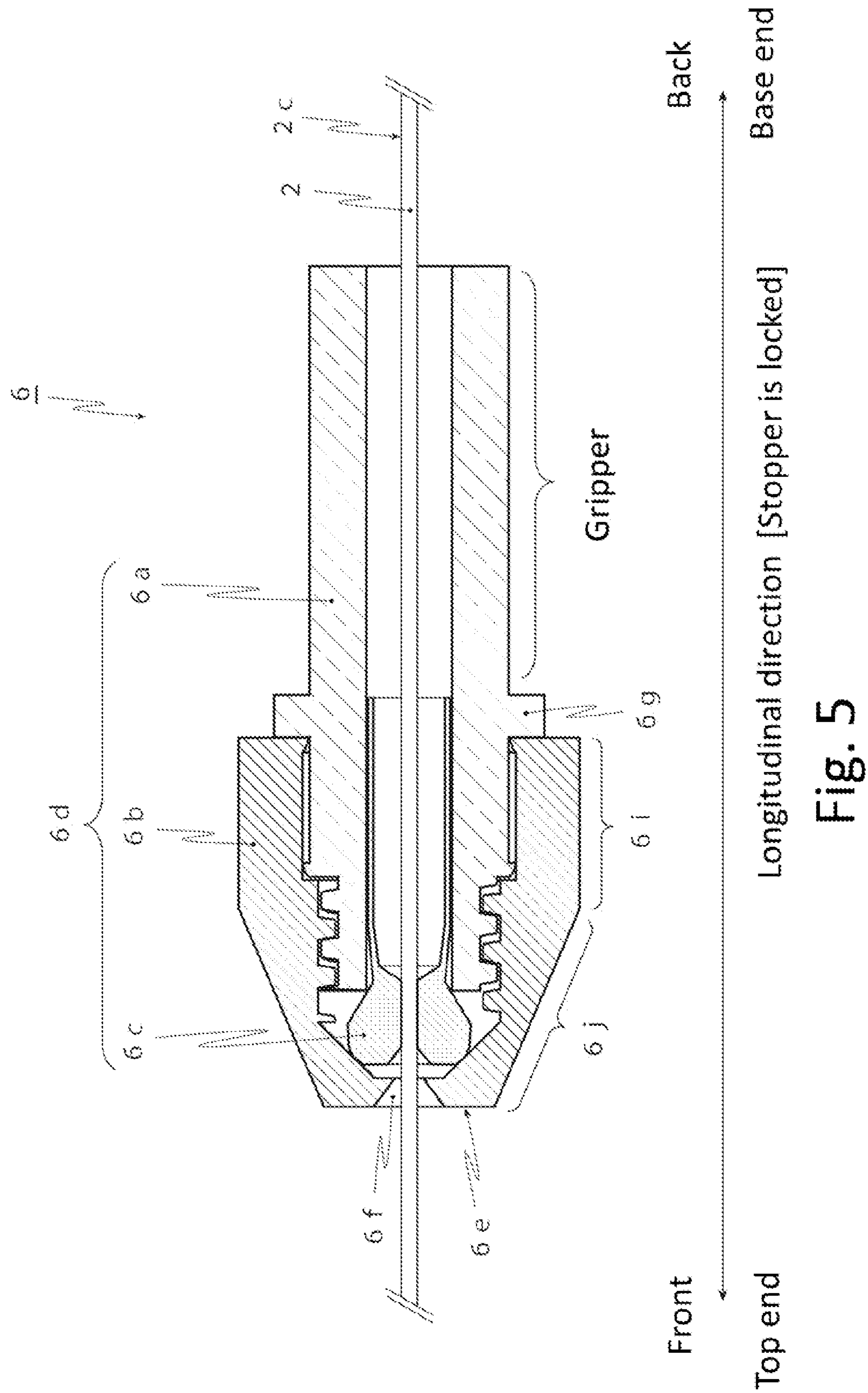
FIG. 5 is an enlarged cross-sectional side view illustrating the state where the stopper of the trapping balloon catheter according to one embodiment of the present invention is locked.

The contour of the tightening cap 6*b* has a base end 6*i* with a shape of a cylinder and a top end part 6*j* with a shape of a circular truncated cone, the diameter of which decreases from the base end 6*i* toward the top end (refer to FIG. 5). On the outer periphery of the tightening cap 6*b*, four ribs 6*k* are formed at intervals of 90° (refer to FIGS. 1 to 3). This facilitates the tightening cap 6*b* to be held when the tightening cap 6*b* is spirally attached. Moreover, this facilitates the rotating (torque) of the trapping balloon catheter 1 by gripping the base end 6*i* of the tightening cap 6*b*. The tightening cap 6*b* is formed of a transparent material to allow the user to easily see the marker M1 or M2 described later when the stopper 6 is locked.

Figure 4:
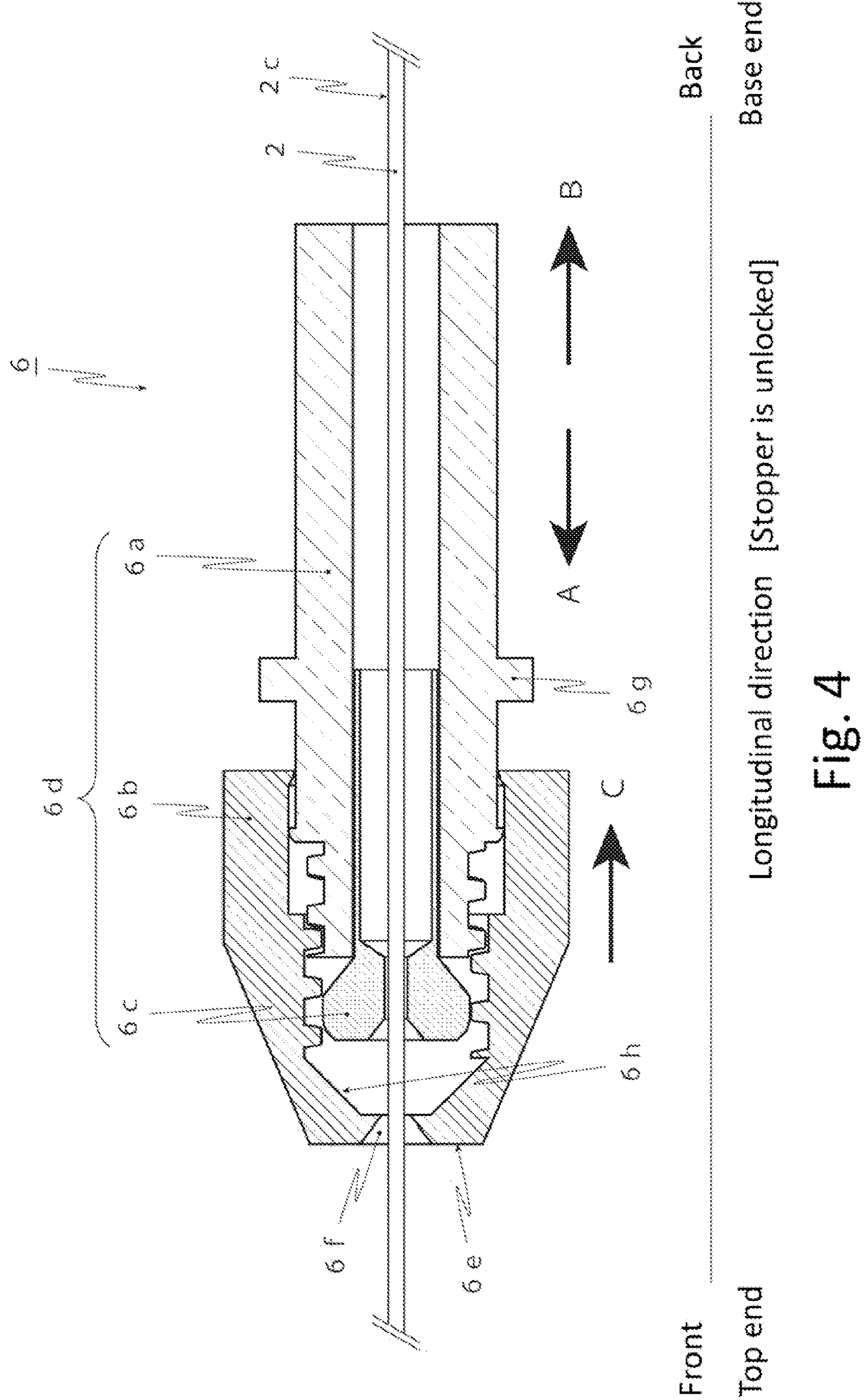
FIG. 4 is an enlarged cross-sectional side view illustrating the state where the stopper of the trapping balloon catheter according to one embodiment of the present invention is unlocked.

In FIG. 4, the expandable and shrinkable part of tightening elastic member 6*c* is not pressed in the diameter direction, and the stopper 6 slidably moves on the outer periphery 2*c* of the catheter shaft 2 in the longer direction. (The stopper 6 is unlocked. Refer to arrows A, B of FIG. 4). When the tightening cap 6*b* spirally attached to move (refer to arrow C of FIG. 4), the expandable and shrinkable part of the tightening elastic member 6*c* is pressed in the diameter direction by the taper wall 6*h* of the tightening cap 6*b* (refer to FIG. 5). When the expandable and shrinkable part presses the catheter shaft 2 from the four directions, the stopper 6 is fixed at a predetermined position in the longer direction of the catheter shaft 2. (The stopper 6 is locked.)

As described above, in the embodiment, the gripper member 6*a*, the tightening cap 6*b*, and the tightening elastic member 6*c* compose a lock mechanism 6*d*, the lock mechanism 6*d* being locked to fix at a predetermined position in the longitudinal direction of the catheter shaft 2, the lock mechanism 6*d* being unlocked to slidably move on the outer periphery 2*c* of the catheter shaft 2 in the longitudinal direction. Moreover, in the embodiment, a simple collet chuck as described above is adopted as the lock mechanism 6*d*.

Figure 7:
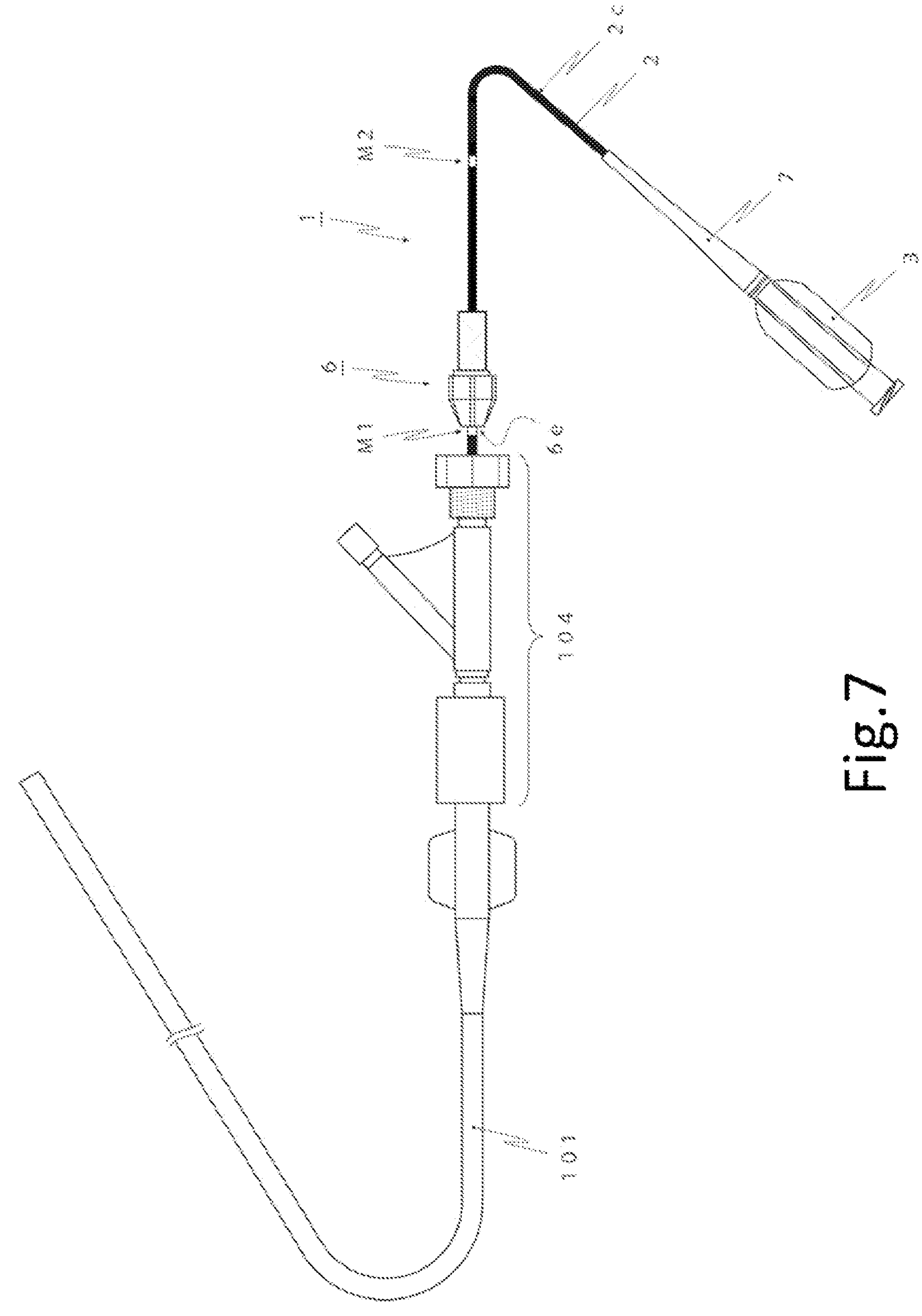
FIG. 7 is a side view illustrating the state in which the catheter shaft of the trapping balloon catheter according to one embodiment of the present invention is inserted in the lumen of the guiding catheter.

As shown in FIGS. 4, 5, and 7, the stopper 6 is provided with a circular abutting part 6*e* abutting the back end of a Y-shaped connector (connection device) 104 placed at the base end of the guiding catheter 101.

As described above, the stopper 6 is able to adjust the insertion length (effective length) of the trapping balloon catheter 1 into the lumen 101*a* of the guiding catheter 101 by changing the locked position.

The configuration of the trapping balloon catheter 1 of the embodiment has a stopper 6 being placed on the outer periphery 2*c* of the catheter shaft 2, the stopper 6 (length adjusting function) adjusting the insertion length (effective length) of the trapping balloon catheter 1 into the lumen 101*a* of the guiding catheter 101 by changing the locked position. Accordingly, the trapping balloon catheter 1 is adaptable for guiding catheters 101 with different effective lengths. As the result, the trapping balloon catheter 1 can attempt to decrease the cost as a whole without the need to increase the type of trapping balloon catheter 1 with different effective lengths. The stopper 6 as the length adjustment function is simply provided with a lock mechanism 6*d*, the lock mechanism 6*d* being locked to fix at a predetermined position in the longitudinal direction of the catheter shaft 2, the lock mechanism 6*d* being unlocked to slidably move on the outer periphery 2*c* of the catheter shaft 2 in the longitudinal direction; a gripper being gripped in back-and-forth moving operation and rotating (torque) operation by pushing, etc., of the trapping balloon catheter 1; and an abutting part 6*e* abutting the back end of a Y-shaped connector (connection device) 104 placed at the base end of the guiding catheter 101. Accordingly, the trapping balloon catheter can suppress the manufacturing cost. Since the catheter shaft 2 of the trapping balloon catheter 1 is very thin, the back-and-forth operation and the rotating (torque) operation by pushing, etc., is difficult. However, these operations are facilitated by gripping the gripper of the stopper 6 with a large diameter. On the other hand, since the diameter of the slidable member (stopper) of Patent Document 1 is small, the back-and-forth operation and the rotating (torque) operation by pushing, etc., is not easy but difficult still even by gripping the stopper. Therefore, according to this configuration, the trapping balloon catheter 1 can be adapted for guiding catheters 101 with different effective lengths, and the trapping balloon catheter 1 with excellent operability can be provided at low cost.

Moreover, the configuration can prevent the balloon 5 of the trapping balloon catheter 1 from popping out from the top end of the guiding catheter 101 because the stopper 6 stops and abuts the back end of a Y-shaped connector (connection device) 104 placed at the base end of the guiding catheter 101. As the result, the function of the trapping balloon catheter 1 that biases and fixes a guide wire 102 to the inner periphery 101*b* of the guiding catheter 101 can always be fulfilled (refer to FIGS. 8A-8B).

As shown in FIGS. 4 and 5, the stopper 6 is further provided with a through-hole 6*f* into which the catheter shaft 2 penetrates. Moreover, according to this configuration, the stopper 6 can always be maintained on the catheter shaft 2. As the result, the stopper 6 can be prevented from falling off from the catheter shaft 2 and always be equipped. The diameter of through-hole 6*f* is 0.5 mm or more and 1.0 mm or less, preferably approximately 0.8 mm. Accordingly, the distance between the inner periphery of the through-hole 6*f* of the stopper 6 and the outer periphery of the catheter shaft 2 can be an appropriate length, and the stopper 6 can be not unstably but smoothly moved. The radius of the abutting part 6*e* is larger than that of the inner periphery of the back end of a Y-shaped connector (connection device) 104 placed at the base end of the guiding catheter 101. According to this configuration, the stopper 6 can surely abut the back end of the Y-shaped connector (connection device) 104 placed at the base end of the guiding catheter 101. As the result, the stopper 6 does not physically enter the Y-shaped connector (connection device) 104 so that the stopper function of the stopper 6 can be more surely fulfilled. Specifically, the inner radius of the back end of the Y-shaped connector 104 (connection device) is 2.5 mm or less, and the radius of the abutting part 6*e* is approximately 3 mm. On the other hand, since the diameter of the stopper of Patent Document 1 is small, the stopper enters some types of the Y-shaped connector in the proximal part of the guiding catheter (especially, when the hemostasis valve of a Y-shaped connector is opened). This may not fulfill the stopper function.

The length in the longer direction of the gripper of the gripper member 6*a* is 5 mm or more. According to this configuration, the back-and-forth operation and the rotating (torque) operation by pushing, etc., of the trapping balloon catheter 1 is facilitated so that the operability of the trapping balloon catheter 1 can be more improved. Specifically, the length in the longer direction of the gripper (the length from the base end of the gripper member 6*a* to the flange 6*g*) is approximately 15 mm. As described above, the base end 6*i* of the tightening cap 6*b* can function as a gripper, and the length in the longer direction of base end 6*i* is approximately 6 mm.

As shown in FIGS. 1 to 3, a position with a predetermined length L1 from the front end 2*b* of the catheter shaft 2 is marked with the marker M1, and a position with a predetermined length L2 which is longer than the predetermined length L1 from the front end 2*b* of the catheter shaft 2 is marked with the marker M2. According to this configuration, the insertion length (effective length) of the trapping balloon catheter 1 into the lumen 101*a* of the guiding catheter 101 (refer to FIGS. 7 and 8A-8B) can be easily changed only by moving and fixing the top end of the stopper 6 to either the marker M1 or M2. FIG. 3 shows that the stopper 6 is fixed to a position which the strain relief 7 enters. This can secure the effective length when arteriosclerotic developed in a femoral artery, an iliac artery, a popliteal artery, a below-the-knee artery, etc., is treated. The configuration may secure the effective length without the strain relief 7 entering the stopper 6 or the effective length L2 with the strain relief 7 entering the stopper 6.

The catheter shaft 2 is formed from a flexible material. Examples of the material of the catheter shaft 2 include stainless steel and polyamide. The outside diameter of the catheter shaft 2 is 1.7 Fr (0.55 mm), and the total length L (from the back end 2*a* to the front end 2*b* (effective length)) is 1170 mm. The total length L3 of the trapping balloon catheter 1 (from the back end of the hub 3 to the front end 2*b* of the catheter shaft 2) is 1264 mm. The predetermined length L1 from the front end 2*b* of the catheter shaft 2 is set to 90 cm, assuming that the guiding catheter 101 with an effective length of 90 cm is used. The predetermined length L2 from the front end 2*b* of the catheter shaft 2 is set to 100 cm, assuming that the guiding catheter 101 with an effective length of 100 cm is used. Specifically, the catheter shaft 2 of the embodiment, the part except the top end region is formed from stainless steel, and the top end region is formed from polyamide. In this case, PTFE coating (black color) is applied to the stainless steel (silver color) except the vicinity of the top end region and the markers M1 and M2 to show the top end region part and the markers M1 and M2 part more prominently than the other parts.

The balloon 5 is also formed from a flexible material. Examples of the material of the balloon 5 include polyamide. The recommended inflation pressure of the balloon 5 is 8 atm (0.8 MPa), and the maximum inflation pressure is 14 atm (1.4 MPa). The outside diameter of the balloon at the recommended inflation pressure is 2.75 mm, and the effective length of the balloon is 20 mm. For example, a diluted contrast agent (the mixture of a contrast agent and saline) is used as a balloon inflation medium.

Examples of the material of each member that composes the stopper 6 are described below. Preferably, the materials of the gripper member 6*a*, the tightening cap 6*b*, and the tightening elastic member 6*c* are polypropylene, polycarbonate, and brass (free-cutting brass rod), respectively.

Use of Trapping Balloon Catheter

The use of the trapping balloon catheter according to one embodiment of the present invention is described below with reference to FIGS. 9A-9G and 10H-10L. The trapping balloon catheter 1 of the embodiment is used to assist exchange of catheters in percutaneous transluminal coronary angioplasty (PTCA) which is a less invasive procedure using a catheter. In PTCA, a catheter for diagnosis and a catheter for treatment are exchanged for each other in a guiding catheter while a blood vessel, etc., is treated.

Preparation Before Operation

Air is removed from the balloon 5 and the lumen for balloon inflation of the trapping balloon catheter 1 by following the procedure described below.

Figure 6:
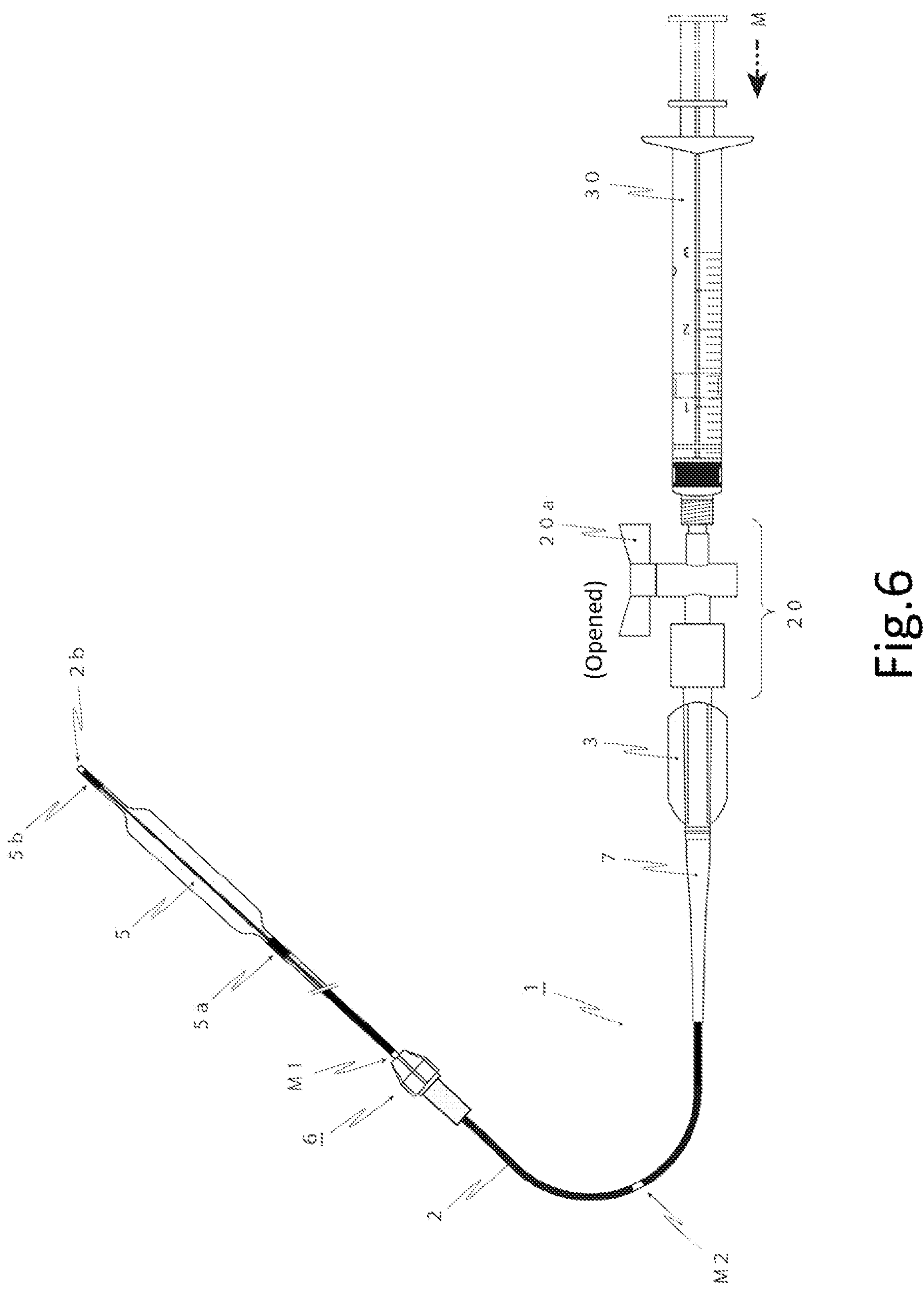
FIG. 6 is a side view illustrating the state where a syringe for balloon inflation is attached to the back end of the trapping balloon catheter according to one embodiment of the present invention through a one-way cock.

(a) As shown in FIG. 6, a syringe for balloon inflation 30, in which a diluted contrast agent as a balloon inflation medium is injected, is attached to the one-way cock 20 connected with the hub 3, and the front end 2*b* of the trapping balloon catheter 1 is aimed downward.

(b) After applying negative pressure enough by the syringe for balloon inflation 30, the negative pressure is slowly released, and the balloon 5 and the lumen for balloon inflation of the trapping balloon catheter 1 are filled with the diluted contrast agent to remove the air.

(c) The above-mentioned step (b) is repeated to completely remove air from the balloon 5 and the lumen for balloon inflation of the trapping balloon catheter 1.

(d) The syringe for balloon inflation 30 is detached from the one-way cock 20 connected with the hub 3 to remove air from the syringe for balloon inflation 30.

(e) The syringe for balloon inflation 30 is attached to the one-way cock 20 connected with the hub 3 again, and negative pressure is applied. After it is confirmed that air does not return to the syringe for balloon inflation 30, the negative pressure is slowly released.

Insertion of Trapping Balloon Catheter, Exchange of Catheters, and Removal of Trapping Balloon Catheter As shown in FIGS. 1 and 2, the top end of the stopper 6 is matched and fixed (locked) at either the marker M1 or M2 depending on the effective length (90 cm or 100 cm) of the guiding catheter 101 to be used (refer to FIG. 7). The one-way cock 20 is attached to the syringe for balloon inflation 30, and the diluted contrast agent is introduced. To prevent the introduced diluted contrast agent from being substituted with air, the cock 20*a* of the one-way cock 20 is closed (refer to FIG. 6).

Figure 9A:
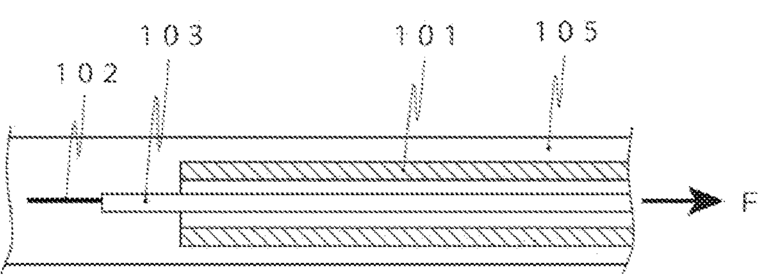
FIGS. 9A-9G are a process chart to explain how to remove a catheter by using the trapping balloon catheter according to one embodiment of the present invention.
Figure 9B:
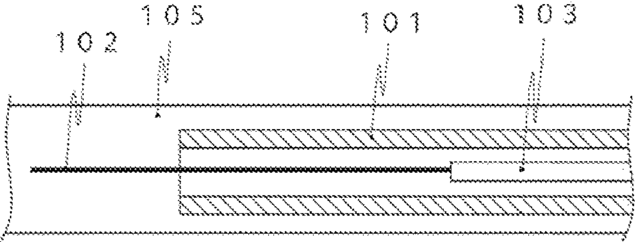

As shown in FIGS. 9A and 9B, while the guide wire 102 is fixed, the hub of a catheter 103 (e.g., OTW (Over The Wire) catheter) is drawn back enough into the guiding catheter 101 until it comes to the vicinity of the back end of the guide wire 102 (refer to the arrow F of FIG. 9A).

Figure 9C:
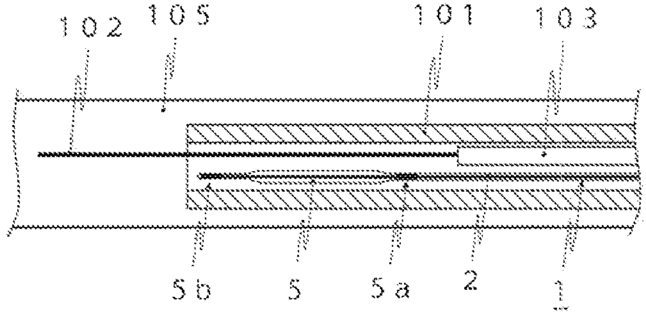

As shown in FIGS. 7, 8A, and 9C, while the OTW catheter 103 is fixed, the trapping balloon catheter 1 is inserted into the guiding catheter 101 under X-ray illumination, and the abutting part 6*e* of the stopper 6 is brought to abut the back end of a Y-shaped connector (connection device) 104 placed at the base end of the guiding catheter 101. At this time, it is confirmed that the X-ray impermeable marker 5*a* in the proximal side of the balloon 5 of the trapping balloon catheter 1 is distally located from the top end of the OTW catheter 103.

Figure 9D:
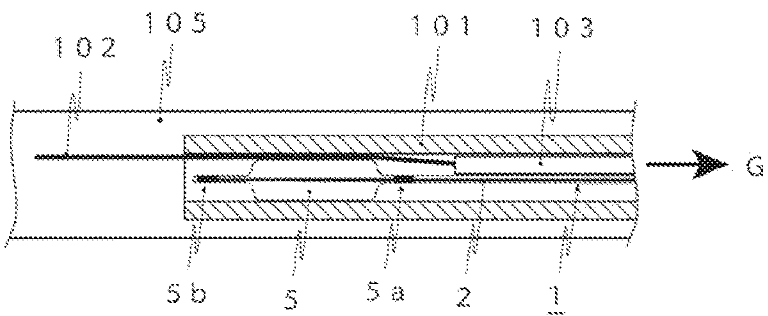

As shown in FIG. 6, the one-way cock 20 attached to the syringe for balloon inflation 30 in which the diluted contrast agent is introduced is connected with the base end opening of the hub 3 of the trapping balloon catheter 1. As shown in FIGS. 6, 8B, and 9D, the cock 20*a* of the one-way cock 20 is opened, and the diluted contrast agent is injected with the syringe for balloon inflation 30 (refer to the chain double-dashed arrow M of FIG. 6) to inflate the balloon 5 of the trapping balloon catheter 1. As the result, the guide wire 102 is biased and fixed to the inner periphery 101*b* of the guiding catheter 101. At this time, the hand part of the guide wire 102 is lightly pulled to confirm that the guide wire 102 is fixed. If the guide wire 102 is not fixed enough, pressure is applied not to exceed the maximum inflation pressure of 14 atm (1.4 MPa) of the balloon 5 until the guide wire 102 is fixed enough. Once the guide wire 102 is fixed enough, the diluted contrast agent is stopped to be introduced, and the cock 20*a* of the one-way cock 20 is closed.

Figure 9E:
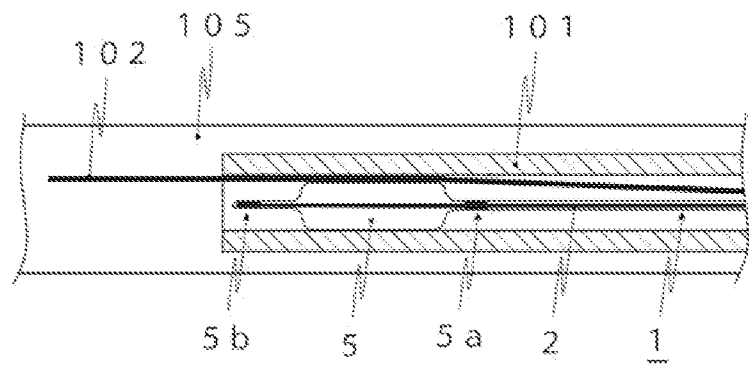

As shown in FIGS. 9D and 9E, while it is observed under X-ray illumination that the position of the guide wire 102 is maintained, the OTW catheter 103 is slowly removed (refer to the arrow G of FIG. 9D).

Figure 9F:
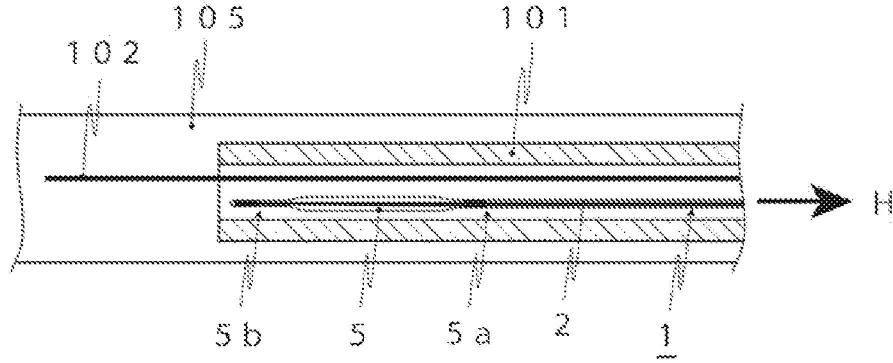

As shown in FIGS. 6 and 9F, the cock 20*a* of the one-way cock 20 is opened, and negative pressure is applied to the syringe for balloon inflation 30 to deflate the balloon 5 of the trapping balloon catheter 1. At this time, it is confirmed under X-ray illumination that the balloon 5 is deflated completely.

Figure 9G:
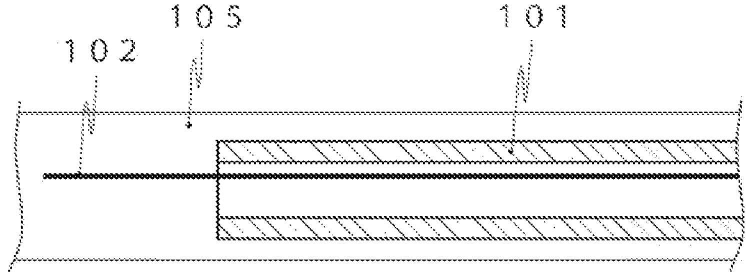

As shown in FIGS. 9F and 9G, the position of the guide wire 102 is maintained, and the trapping balloon catheter 1 is carefully, slowly removed from the guiding catheter 101 without excessive power applied while the balloon 5 of the trapping balloon catheter 1 is completely deflated (refer to the arrow H of FIG. 9F).

After it is confirmed that there is flashback from the Y-shaped connector (connection device) 104 shown in FIG. 7 to remove air from the guiding catheter 101, the following step is performed.

If insertion (exchange) of another OTW catheter or a monorail catheter is necessary after removal of the OTW catheter 103, the balloon 5 of the trapping balloon catheter 1 is inflated as shown in FIG. 9E to keep basing and fixing the guide wire 102 to the inner periphery 101*b* of the guiding catheter 101 (refer to FIGS. 8A-8B).

Figure 10H:
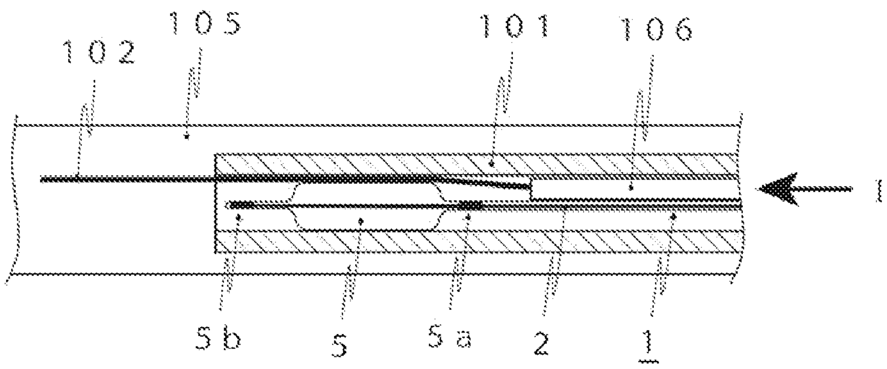
FIGS. 10H-10L are a process chart to explain how to insert a catheter (exchange catheters) by using the trapping balloon catheter according to one embodiment of the present invention.

As shown in FIG. 10H, another OTW catheter 106 is slowly inserted into the vicinity of the X-ray impermeable marker 5*a* in the proximal side of the balloon 5 of the trapping balloon catheter 1 along the guide wire 102 (refer to the arrow I of FIG. 10H).

Figure 10I:
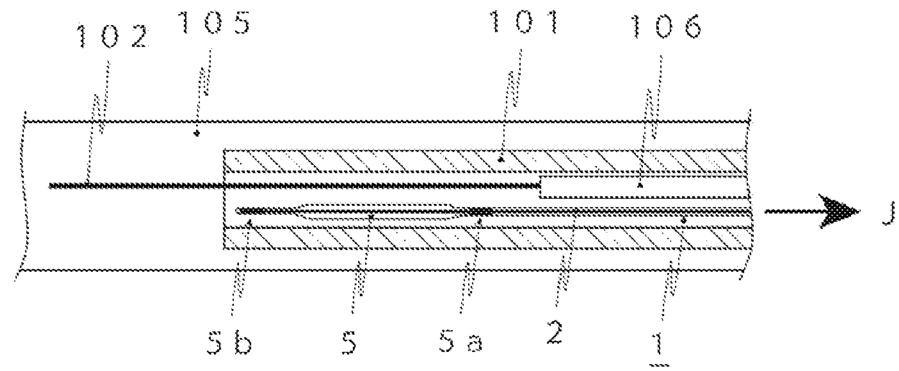

As shown in FIGS. 6 and 10I, the cock 20*a* of the one-way cock 20 is opened, and negative pressure is applied to the syringe for balloon inflation 30 to deflate the balloon 5 of the trapping balloon catheter 1. At this time, it is confirmed under X-ray illumination that the balloon 5 is deflated completely.

Figure 10J:
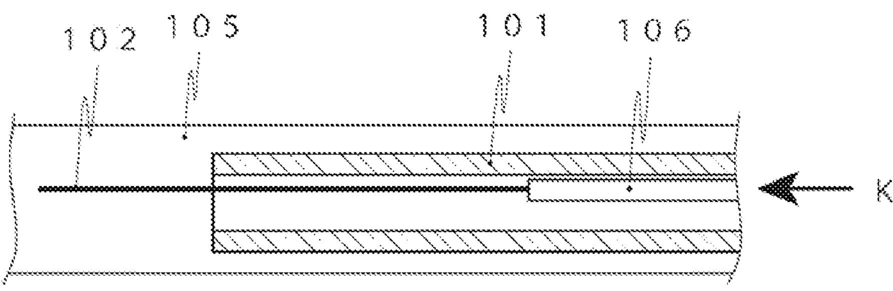

As shown in FIGS. 10I and 10J, the position of the guide wire 102 is maintained, and the trapping balloon catheter 1 is carefully, slowly removed from the guiding catheter 101 without excessive power applied while the balloon 5 of the trapping balloon catheter 1 is completely deflated (refer to the arrow J of FIG. 100.

Figure 10K:
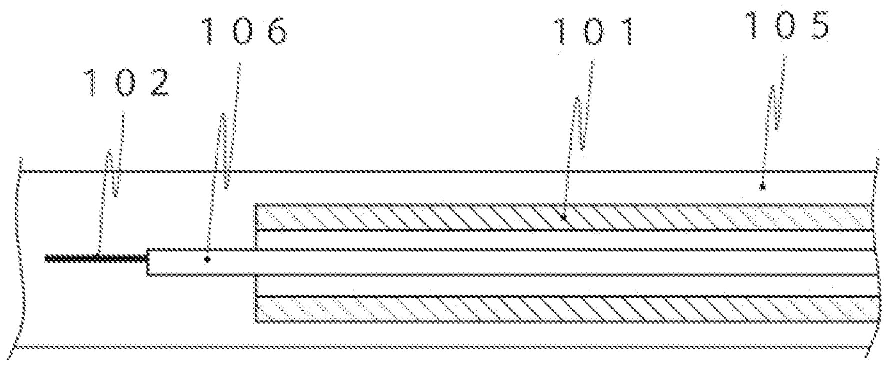

As shown in FIGS. 10I and 10K, while the guide wire 102 is fixed, the OTW catheter 106 is pushed (refer to the arrow K of FIG. 10J) to project the OTW catheter 106 from the top end of the guiding catheter 101.

Figure 10L:
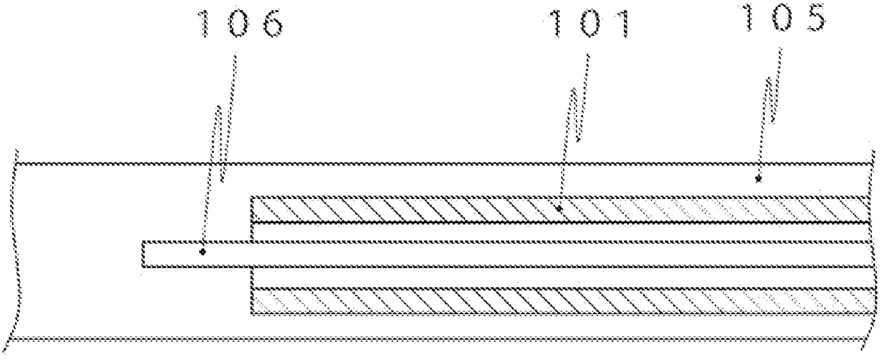

As shown in FIGS. 10K and 10L, while the OTW catheter 106 is fixed, the guide wire 102 is slowly removed. The exchange of catheters is now completed.

The embodiment has been explained, giving an example of the collet chuck stopper 6 provided with a gripper member 6*a* that is approximately cylindrically formed, a tightening cap 6*b* that is spirally attached to the top end of the gripper member 6*a*, and a tightening elastic member 6*c*, the stopper 6 being fixed at a predetermined position in the longer direction of the catheter shaft 2 when the tightening cap 6*b* spirally attached to move, and the tightening elastic member 6*c* is pressed in the diameter direction by the taper wall 6*h* on the front inner periphery. However, the present invention is not limited to such a configuration. The aspects of the stopper may be as shown in FIGS. 11A-11B and 12A-12B, for example.

Figure 11A:
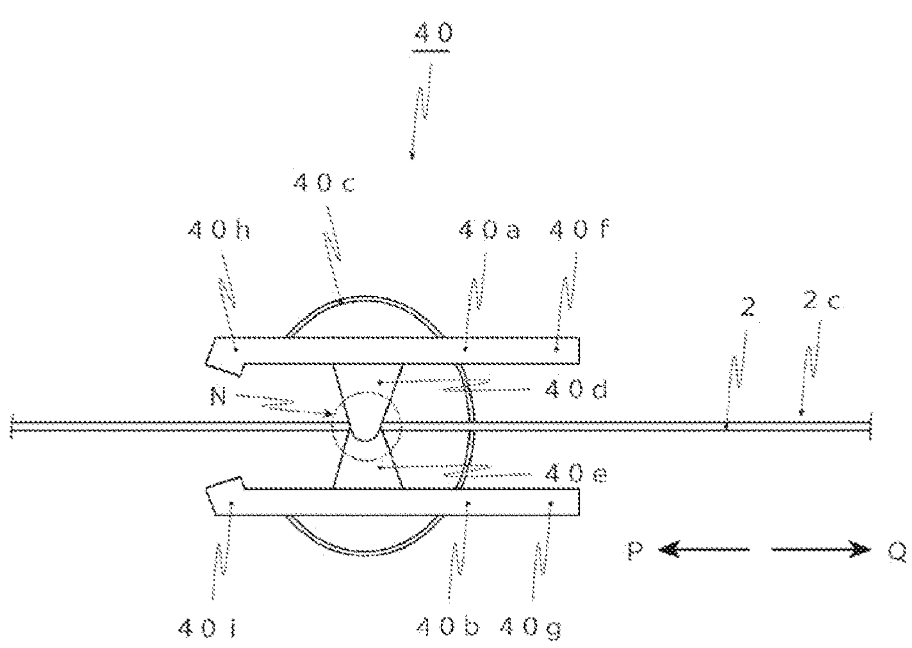
FIGS. 11A-11B are a schematic side view illustrating another aspect of the stopper as a component of the trapping balloon catheter according to one embodiment of the present invention.
Figure 11B:
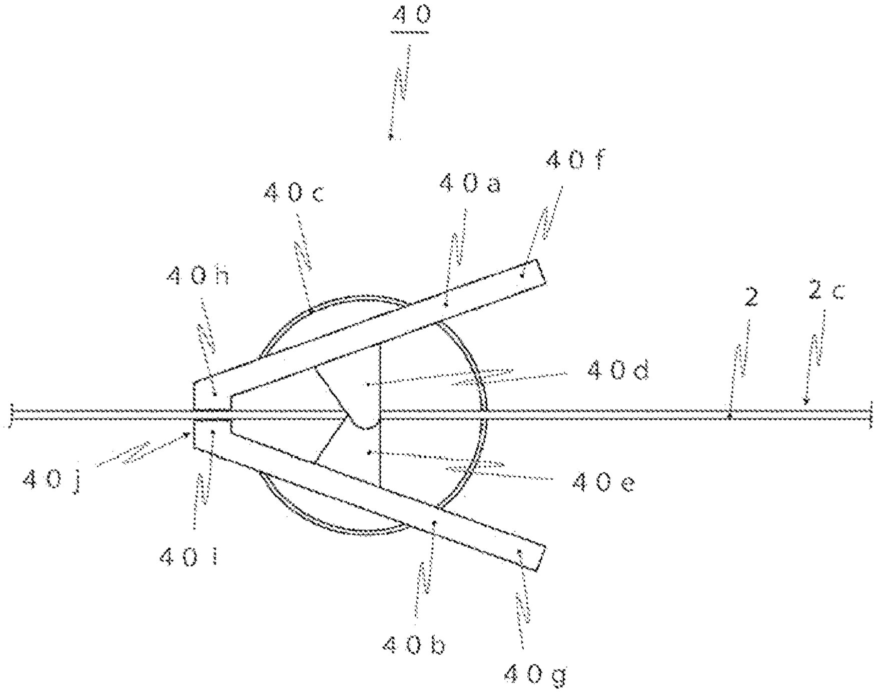

The stopper 40 shown in FIGS. 11A-11B is "a clothespin form". As shown in FIGS. 11A-11B, the stopper 40 is provided with a pair of fastening pieces 40*a*, 40*b* and a biasing means 40*c*. The pair of fastening pieces 40*a*, 40*b* are rotatably connected with each other through support shafts 40*d*, 40*e* which have respective picking parts 40*g* formed at the first end and respective pinching parts 40*h*, 40*i* formed at the second end. The biasing means 40*c* consists of a C-shaped spring member, which is placed between the pair of fastening pieces 40*a*, 40*b*. The biasing means 40*c* biases the pair of fastening pieces 40*a* and 40*b* to enter the close state in which the pinching parts 40*h*, 40*i* abut each other. A through-hole (not shown in the attached drawing) into which the catheter shaft 2 penetrates is formed at the axis N of the support shafts 40*d*, 40*e*. According to this configuration, the stopper 40 can always be maintained on the catheter shaft 2 so that the stopper 40 can be prevented from falling off from the catheter shaft 2 and always be equipped. The pair of fastening pieces 40*a*, 40*b* function as a gripper gripped for the back-and-forth movement operation and the rotating (torque) operation by pushing, etc., of the trapping balloon catheter 1. The stopper 40 is provided with an abutting part 40*j* abutting the back end of a Y-shaped connector (connection device) 104 (refer to FIG. 7) placed at the base end of the guiding catheter 101. According to this configuration, the stopper 40 can abut the back end of the Y-shaped connector (connection device) 104 placed at the base end of the guiding catheter 101 to surely fulfill the stopper function of the stopper 40.

In FIG. 11A showing that the picking parts 40*f*, 40*g* are pinched by the user's thumb and forefinger, the pinching parts 40*h*, do not hold the catheter shaft 2, and the stopper 40 slidably moves on the outer periphery 2*c* of the catheter shaft 2 in the longer direction. (The stopper 40 is unlocked. Refer to arrows P, Q of FIG. 11A.) When the fingers are disengaged from the picking parts 40*f*, the biasing means 40*c* biases the pair of fastening pieces 40*a* and to enter the close state in which the pinching parts 40*h*, 40*i* abut each other (as shown in FIG. 11B), and the stopper 40 is fixed at a predetermined position in the longer direction of the catheter shaft 2. (The stopper 40 is locked.)

As described above, the stopper 40 is provided with a lock mechanism, the lock mechanism being locked to fix at a predetermined position in the longitudinal direction of the catheter shaft 2, the lock mechanism being unlocked to slidably move on the outer periphery 2*c* of the catheter shaft 2 in the longitudinal direction.

Figure 12A:
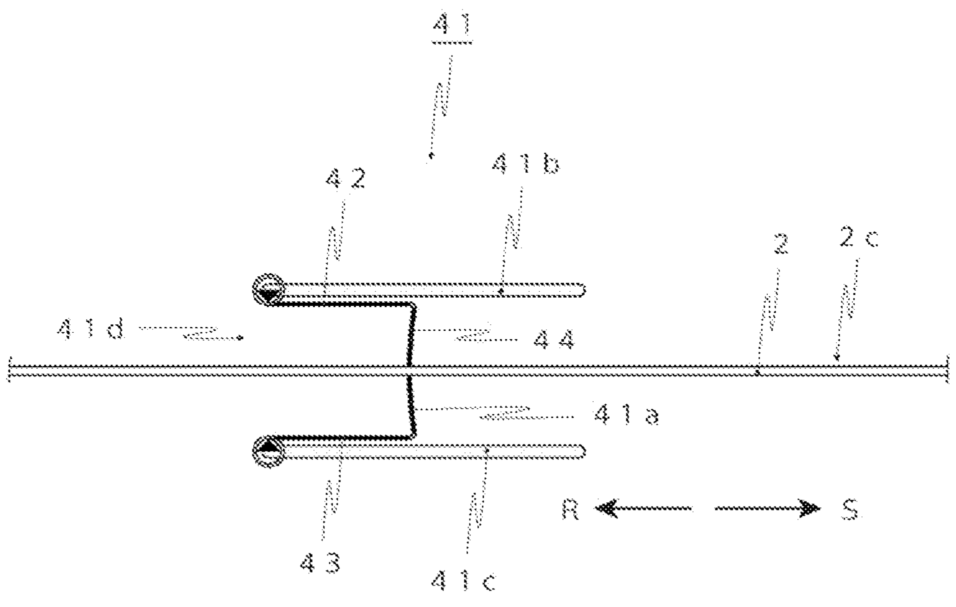
FIGS. 12A-12B are a schematic side view illustrating another aspect of the stopper as a component of the trapping balloon catheter according to one embodiment of the present invention.
Figure 12B:
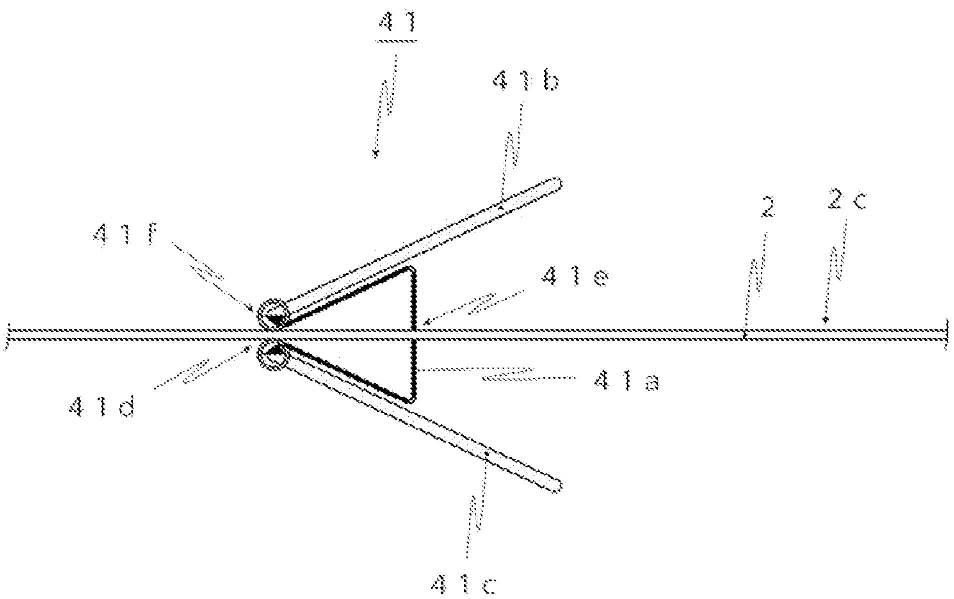

The stopper 41 shown in FIGS. 12A-12B is "a fold-back clip form". As shown in FIGS. 12A-12B, the stopper 41 is provided with a stopper main body 41*a* and a pair of picking pieces 41*b*, 41*c*. The stopper main body 41*a* is provided with two plate parts 42, 43 placed opposite to each other and a base plate part 44 connecting the plate parts 42, 43. The edges of the plate parts 42, 43 compose a pinching part 41*d*, which is configured to snap and abut each other and open by the pair of picking pieces 41*b*, 41*c*. A through-hole 41*e* into which the catheter shaft 2 penetrates is formed in the base plate part 44 of the stopper main body 41*a*. According to this configuration, the stopper 41 can always be maintained on the catheter shaft 2. As the result, the stopper 41 can be prevented from falling off from the catheter shaft 2 and always be equipped. The stopper main body 41*a* functions as a gripper gripped for the back-and-forth movement operation and the rotating (torque) operation by pushing, etc., of the trapping balloon catheter 1. The stopper 41 is provided with an abutting part 41*f* abutting the back end of a Y-shaped connector (connection device) 104 (refer to FIG. 7) placed at the base end of the guiding catheter 101. According to this configuration, the stopper 41 can abut the back end of the Y-shaped connector (connection device) 104 placed at the base end of the guiding catheter 101 to surely fulfill the stopper function of the stopper 41.

In FIG. 12A showing that the picking pieces 41*b*, 41*c* are pinched by the user's thumb and forefinger, the pinching part 41*d* of the stopper main body 41*a* do not hold the catheter shaft 2, and the stopper 41 slidably moves on the outer periphery 2*c* of the catheter shaft 2 in the longer direction. (The stopper 41 is unlocked. Refer to arrows R, S of FIG. 12A). When the fingers are disengaged from the pair of picking pieces 41*b*, 41*c*, the edges of the plate parts 42, 43 (composing the pinching part 41*d*) of the stopper main body 41*a* snap and abut each other (as shown in FIG. 12B), and the stopper 41 is fixed at a predetermined position in the longer direction of the catheter shaft 2. (The stopper 41 is locked.)

As described above, the stopper 41 is provided with a lock mechanism being locked to fix at a predetermined position in the longitudinal direction of the catheter shaft 2, the lock mechanism being unlocked to slidably move on the outer periphery 2*c* of the catheter shaft 2 in the longitudinal direction.

The embodiment has also been explained, giving an example where the catheter shaft 2 is connected with the hub 3 through the strain relief (anti-kink protector) 7. However, the present invention is not limited to such a configuration. The trapping balloon catheter of the present invention may not necessarily be provided with a strain relief (anti-kink protector).

The embodiment has also been explained, giving an example where the stopper 6 is provided with an abutting part 6*e* abutting the back end of a Y-shaped connector (connection device) 104 placed at the base end of the guiding catheter 101. However, the present invention is not limited to such a configuration. The Y-shaped connector (connection device) 104 is optionally provided, and the abutting part 6*e* of the stopper 6 may abut the base end of the guiding catheter 101. On the basis of ISO standard, the inner diameter of the base end of the guiding catheter 101 is 4.3 mm, and the diameter of the abutting part 6*e* of the stopper 6 is approximately 6 mm.

The embodiment has also been explained, giving an example where the connection device is a Y-shaped connector 104. However, the present invention is not limited to such a configuration. For example, a T-shaped connector, etc., is assumed to be used as the connection device in place of a Y-shaped connector 104.

The embodiment has also been explained, giving an example of the stopper 6 provided with a circular abutting part 6*e* and a through-hole 6*f* into which the catheter shaft 2 penetrates. However, the present invention is not limited to such a configuration. For example, the shape of the abutting part of the stopper may be an oval, a rectangular, etc., other than a circle. In this case, the length of a part of the abutting part where the length from the through-hole to the outer edge is maximized only has to be larger than the inner radius of the back end of the connection device placed at the base end of the guiding catheter and/or the inner radius of the base end of the guiding catheter. According to this configuration, the stopper can surely abut the back end of the connection device placed at base end of the guiding catheter or the base end of the guiding catheter. As the result, the stopper function of the stopper can be more surely fulfilled.

DESCRIPTION OF REFERENCE NUMERALS

1: trapping balloon catheter, 2: catheter shaft, 2*a*: back end, 2*b*: front end, 2*c*: outer periphery, 3: hub, 5: balloon, 5*a*, 5*b*: X-ray impermeable marker. 6, 40, 41: stopper, 6*a*: gripper member, 6*b*: tightening cap, 6*c* tightening elastic member, 6*d*: lock mechanism, 6*e*, abutting part, 6*f*, 41*e*: through-hole, 6*g*: flange, 6*h*: taper wall, 7 strain relief (anti-kink protector), 20: one-way cock, 30: syringe for balloon inflation, 40*a*, 40*b*: fastening piece, 40*c*: biasing means, 40*d*, support shaft, 40*f*, 40*g*: picking part, 40*h*, 40*i*, 41*d*: pinching part, 41*a*: stopper main body, 41*b*, 41*c*: picking piece, 42, 43: plate part, 44: base plate part, 101: guiding catheter, 101*a*: lumen, 101*b*: inner periphery, 102: guide wire, 103, 106: (OTW) catheter, 104: Y-shaped connector (connection device), 105: blood vessel, N: axis

What is claimed is:

1. A trapping balloon catheter for assisting insertion and/or removal of a catheter, the trapping balloon catheter being insertable in a lumen of a guiding catheter, the trapping balloon catheter biasing and fixing a guide wire to an inner periphery of the guiding catheter, the trapping balloon catheter comprising:

a catheter shaft having a front end and a back end, the catheter shaft being formed to have a predetermined total length L from the back end to the front end, wherein the back end is connected with a hub through a strain relief;

a balloon being placed in a front end region of the catheter shaft, the balloon being inflatable in the lumen of the guiding catheter to bias and fix the guide wire to the inner periphery of the guiding catheter; and a stopper for adjusting an insertion length in which the trapping balloon catheter is inserted into the lumen of the guiding catheter, wherein the stopper includes;

a through-hole penetrating the catheter shaft;

a lock mechanism being placed on an outer periphery of the catheter shaft, the lock mechanism being locked to fix at a predetermined position in a longitudinal direction of the catheter shaft and a position which the strain relief enters, the lock mechanism being unlocked to slidably move on the outer periphery of the catheter shaft in the longitudinal direction;

a gripper being grippable in back-and-forth moving operation and rotating operation of the trapping balloon catheter; and an abutting part for abutting a back end of a connection device provided at a base end of the guiding catheter and/or abutting the base end of the guiding catheter; and wherein the stopper adjusts the insertion length by changing a locking position of the lock mechanism.

2. The trapping balloon catheter according to claim 1, wherein the through-hole of the stopper has a diameter ranging from 0.5 to 1.0 millimeters (mm).

3. The trapping balloon catheter according to claim 1, wherein a maximum distance from a center of the through-hole to an outer edge is larger than at least one of an inner radius of the back end of the connection device provided at the base end of the guiding catheter and/or an inner radius of the base end of the guiding catheter.

4. The trapping balloon catheter according to claim 1, wherein the gripper has a length of 5 millimeters (mm) or more in the longitudinal direction.

5. The trapping balloon catheter according to claim 1, wherein a position with a predetermined length L1 from the front end of the catheter shaft is marked with a marker M1, and a position with a predetermined length L2 which is longer than the predetermined length L1 from the front end of the catheter shaft is marked with a marker M2.

* * * * *